(12) United States Patent
Horres et al.

(10) Patent No.: US 8,679,520 B2
(45) Date of Patent: Mar. 25, 2014

(54) COATING OF STENTS FOR PREVENTING RESTENOSIS

(75) Inventors: Roland Horres, Stolberg (DE); Michael Hoffmann, Eschweiler (DE); Erika Hoffmann, Eschweiler (DE); Donato Di Biase, Aachen (DE); Volker Faust, Aachen (DE)

(73) Assignee: Hemoteq AG, Wurselen (DE)

( * ) Notice: Subject to any disclaimer, the term of this patent is extended or adjusted under 35 U.S.C. 154(b) by 1831 days.

(21) Appl. No.: 10/493,157

(22) PCT Filed: Oct. 15, 2002

(86) PCT No.: PCT/DE02/03941
§ 371 (c)(1),
(2), (4) Date: Apr. 15, 2004

(87) PCT Pub. No.: WO03/034944
PCT Pub. Date: May 1, 2003

(65) Prior Publication Data
US 2005/0060028 A1  Mar. 17, 2005

(30) Foreign Application Priority Data

Oct. 15, 2001 (DE) .................................. 101 50 340
Nov. 26, 2001 (DE) .................................. 101 57 610

(51) Int. Cl.
*A61F 2/00* (2006.01)
(52) U.S. Cl.
USPC ......................................... 424/426; 424/423
(58) Field of Classification Search
None
See application file for complete search history.

(56) References Cited

U.S. PATENT DOCUMENTS

| | | | |
|---|---|---|---|
| 5,340,932 | A | 8/1994 | Fussi et al. |
| 5,380,299 | A | 1/1995 | Fearnot et al. |
| 5,464,450 | A | 11/1995 | Palme, II et al. |
| 5,980,551 | A | 11/1999 | Summers et al. |
| 6,174,326 | B1 | 1/2001 | Kitaoka et al. |
| 6,299,604 | B1 * | 10/2001 | Ragheb et al. ............... 604/265 |
| 6,355,055 | B1 | 3/2002 | Waksman et al. |
| 6,702,850 | B1 * | 3/2004 | Byun et al. ................... 623/1.44 |

FOREIGN PATENT DOCUMENTS

| | | |
|---|---|---|
| CA | 2 363 119 | 8/2000 |
| EP | 0623354 | 11/1994 |
| EP | 0 608 095 | 5/1999 |
| JP | 3-185001 | 8/1991 |
| JP | 8-191887 | 7/1996 |
| JP | 10151190 | 6/1998 |
| JP | 2002-537075 | 11/2002 |
| WO | WO 91/12779 | 9/1991 |

(Continued)

OTHER PUBLICATIONS

Nelson et al., Endovascular Stents and Stent Grafts: Is heparin coating desirable?, Cardiovascular and Interventional Radiology (2000) 23:252-255.*
Hoffman et al., Endothelial cell surface heparan sulfate and synthetic heparin derivatives as hemocompatible coating for biomaterials, Mat-wiss u Werkstofftech, 32, 110-115 (2001).*

(Continued)

*Primary Examiner* — Anand Desai
*Assistant Examiner* — Melissa Mercier
(74) *Attorney, Agent, or Firm* — Amin, Turocy & Watson, LLP

(57) ABSTRACT

The invention relates to stents with at least one hemocompatible coating which contains an antiproliferative, antiinflammatory and/or antithrombotic active agent, methods for the preparation of said stents as well as the use of said stents for the prevention of restenosis.

8 Claims, 6 Drawing Sheets

(56) References Cited

FOREIGN PATENT DOCUMENTS

| WO | 97/22371 | 6/1997 |
|----|----------|--------|
| WO | 97/49434 | 12/1997 |
| WO | 00/10622 | 3/2000 |
| WO | WO 02/13883 | 2/2002 |
| WO | WO 03/034944 | 5/2003 |

OTHER PUBLICATIONS

Hoffman et al. Endothelial cell surface heparan sulfate and synthetic heparin derivatives as hemocompatible coating for biomaterials, Mat-wis U Werkstoftech, 32, 110-115 9 (2001).*
International Search Report, PCT/DE02/03941, Mar. 27, 2003.
International Preliminary Examination Report, PCT/DE2002/003941, Feb. 12, 2004.

* cited by examiner

COATING OF STENTS FOR PREVENTING RESTENOSIS

This invention relates to stents with a hemocompatible coating and at least a second layer which contains at least an antiproliferative, immunosuppressive, antiinflammatory and/or antithrombotic active agent, methods for the preparation of said stents as well as the use of said stents for the prevention of restenosis.

The implantation of stents using balloon dilatation of occluded vessels increasingly established in the last years. Although stents decrease the risk of a renewed vessel occlusion they are until now not capable of preventing such restenoses completely.

An exact conceptual description of restenosis cannot be found in the technical literature. The most commonly used morphologic definition of the restenosis is the one which defines the restenosis after a successful PTA (percutaneous transluminal angioplasty) as a reduction of the vessel diameter to less than 50% of the normal one. This is an empirically defined value of which the hemodynamic relevance and its relation to clinical pathology lacks of a massive scientific basis. In practical experience the clinical aggravation of a patient is often viewed as a sign for a restenosis of the formerly treated vessel segment.

There are three different reasons for the restenosis caused by the stent:

a.) During the first period after the implantation the stent surface is in direct contact with the blood and an acute thrombosis can occur which again occludes the vessel due to the now present foreign surface.

b.) The implantation of the stent generates vessel injuries which also induce inflammation reactions which play an important role for the recovery process during the first seven days in addition to the above mentioned thrombosis. The herein concurrent processes are among others connected with the release of growth factors which initiate an increased proliferation of the smooth muscle cells which rapidly leads to a renewed occlusion of the vessel, because of uncontrolled growth.

c.) After a couple of weeks the stent starts to grow into the tissue of the blood vessel. This means that the stent is surrounded totally by smooth muscle cells and has no contact to the blood. This cicatrization can be too distinctive (neointima hyperplasia) and may lead to not only a coverage of the stent surface but to the occlusion of the total interior space of the stent.

It was tried vainly to solve the problem of restenosis by the coating of the stents with heparin (J. Whörle et al., European Heart Journal 2001, 22, 1808-1816). Heparin addresses as anti coagulant only the first mentioned cause and is moreover able to unfold its total effect only in solution. This first problem is meanwhile almost totally avoidable medicamentously by application of anti-coagulants. The second and third problem is intended now to be solved by inhibiting the growth of the smooth muscle cells locally on the stent. This is carried out by e.g. radioactive stents or stents which contain pharmaceutically active agents.

U.S. Pat. No. 5,891,108 discloses for example a hollow moulded stent, which can contain pharmaceutical active agents in its interior, that can be released throughout a various number of outlets in the stent. Whereas EP-A-1 127 582 describes a stent that shows ditches of 0.1-1 mm depth and 7-15 mm length on its surface which are suitable for the implementation of an active agent. These active agent reservoirs release similarly to the outlets in the hollow stent the contained pharmaceutically active agent in a punctually high concentration and over a relatively long period of time which however leads to the fact that the smooth muscle cells are not anymore or only very delayed capable of enclosing the stent. As a consequence the stent is much longer exposed to the blood, what leads again to increased vessel occlusions by thromboses (Liistro F., Colombo A., Late acute thrombosis after Paclitaxel eluting stent implantation. Heart 2001, 86, 262-264).

One approach to this problem is represented by the phosphorylcholine coating of biocompatibles (WO 0101957), as here phosphorylcholine, a component of the erythrocyte cell membrane, shall create a non thrombogeneous surface as a component of the coated non biodegradable polymer layer on the stent. Dependent of its molecular weight, thereby the active agent is absorbed by the polymer containing phosphorylcholine layer or adsorbed on the surface.

Object of the present invention is, to provide stents which allow a continuous controlled ingrowth of the stent into the vessel wall on the one hand by suppression of the cellular reactions in the primal days and weeks after implantation by the support of the selected active agents and active agent combinations and on the other hand by providing an athrombogeneous resp. inert resp. biocompatible surface which guarantees that with the decrease of the active agent's influence and the decomposition of the matrix, no reactions to the existing foreign surface take place which also can lead in a long term to a reocclusion of the blood vessel.

This object is solved by the technical teaching of the independent claims of the present invention. Further advantageous embodiments of the invention are evident from the dependent claims, the description as well as the examples.

The stents according to invention are coated with a hemocompatible layer and feature one or more additional layers which at least comprise an antiproliferative and/or antiinflammatory and if needed an antithrombotic active agent.

The hemocompatible coating of a stent provides the required blood compatibility and the active agent (or active agent combination) which is distributed homogeneously over the total surface of the stent provides that the covering of the stent surface with cells especially smooth muscle and endothelial cells takes place in a controlled way. Thus no rapid population and overgrowth with cells takes place on the stent surface which could lead to a restenosis whereas the covering of the stent surface with cells is also not completely prevented by a high medicament concentration which involves the risk of thrombosis.

Thus the incorporation of active agents guarantees that the active agent or the active agent combination which is bound covalently and/or adhesively to the subjacent layer and/or implemented covalently and/or adhesively into the layer is released continuously and in small doses so that the population of the stent surface by cells is not inhibited however an overgrowth is prevented.

This combination of both effects awards the ability to the inventive stent to grow rapidly into the vessel wall and reduces both the risk of restenosis and the risk of thrombosis. The release of one or more active agents spans over a period from 1 to 12 months, preferably 1 to 2 months after implantation.

Antiproliferative substances, antiphlogistic as well as antithrombotic compounds are used as active agents. Preferably cytostatics, macrolide antibiotics and/or statins are used as antiproliferative active agents. Applyable antiproliferative active agents are sirolimus (rapamycin), everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, betulinic acid, camptothecin, lapachol, β-lapachone, podophyllotoxin, betulin, trofosfamide, podophyllic acid 2-ethylhydrazide, ifosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterin, ademetionine, myrtecaine, polidocanol, nonivamide, levomenthol, benzocaine, aescin, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, selectin (cytokine antagonist), CETP inhibitor, cadherines, cytokinin inhibitors, COX-2 inhibitor, NFkB, angiopeptin, ciprofloxacin, camptothecin, fluroblastin, monoclonal antibodies, which inhibit the muscle cell proliferation, bFGF antagonists, probucol, prostaglandins, colchicine, NO donors such as pentaerythritol tetranitrate and syndnoeimines, S-nitrosoderivatives, tamoxifen, β-estradiol, a-estradiol, estrone, estriol, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, paclitaxel and derivatives thereof (6-a-hydroxy-paclitaxel, baccatin, taxotere and other), synthetically produced as well as from native sources obtained macrocyclic oligomers of carbon suboxide (MCS) and derivatives thereof, molgramostim (rhuGM-CSF), peginterferon a-2b, lenograstim (r-HuG-CSF), filgrastim, macrogol, dacarbazine, basiliximab, daclizumab, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, called IGF-1. From the group of antibiotics furthermore cefadroxil, cefazolin, cefaclor, cefotaxim, tobramycin, gentamycin are used. Positive influence on the postoperative phase have also the penicillins such as dicloxacillin, oxacillin, sulfonamides, metronidazol, antithrombotics such as argatroban, aspirin, abciximab, synthetic antithrombin, bivalirudin, coumadin, enoxaparin, hemoparin, tissue plasminogen activator, GpIIb/IIIa platelet membrane receptor, factor $X_a$ inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, caspase inhibitors, apoptosis inhibitors, apoptosis regulators such as p65 NF-kB or Bcl-xL antisense oligonucleotides and prostacyclin, vapiprost, a, β and ? interferon, histamine antagonists, serotonin blockers, halofuginone, nifedipine, tocopherol, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamid, retinoic acid, quinidine, disopyramide, flecainide, propafenone, sotalol, amidorone. Further active agents are steroids (hydrocortisone, betamethasone, dexamethasone), non-steroidal substances (NSAIDS) such as fenoprofen, ibuprofen, indomethacin, naproxen, phenylbutazone and others. Antiviral agents such as acyclovir, ganciclovir and zidovudine are also applyable. Different antimycotics are used in this area. Examples are clotrimazole, flucytosine, griseofulvin, ketoconazole, miconazole, nystatin, terbinafine. Antiprozoal agents such as chloroquine, mefloquine, quinine are effective active agents in equal measure, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, 1,11-dimethoxycanthin-6-one, 1-hydroxy-11-methoxycanthin-6-one, scopoletin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-β-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, vismione A and B, further natural terpenoids such as hippocaesculin, 14-dehydroagrostistachin, agroskerin, agrostistachin, 17-hydroxyagrostistachin, ovatodiolids, 4,7-oxycycloanisomelic acid, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin.

The active agents are used separately or combined in the same or a different concentration. Especially preferred are active agents which feature also immunosuppressive properties besides their antiproliferative effect. Suchlike active agents are erythromycin, midecamycin, tacrolimus, sirolimus, paclitaxel and josamycin. Furthermore preferred is a combination of several antiproliferatively acting substances or of antiproliferative active agents with immunosuppressive active agents. Preferred for the present invention are tacrolimus, paclitaxel and derivatives, trapidil, a- and β-estradiol, macrocyclic carbon suboxide (MCS) as well as derivatives thereof and sirolimus.

The active agent is preferably contained in a pharmaceutical active concentration from 0.001-10 mg per cm² stent surface. Additional active agents can be contained in a similar concentration in the same or in other layers.

The hemocompatible layer which covers directly the stent preferably comprises heparin of native origin as well as synthetically obtained derivatives with different sulphation coefficients (sulphation degrees) and acylation coefficients (acylation degrees) in the molecular weight range of the pentasaccharide which is responsible for the antithrombotic activity up to the standard molecular weight of the purchasable heparin, heparan sulphates and derivatives thereof, oligo- and polysaccharides of the erythrocyte glycocalix, which imitate in a perfect way the athrombogeneous surface of the erythrocytes, since contrary to phosphorylcholine, here the actual contact between blood and erythrocyte surface takes place, oligosaccharides, polysaccharides, completely desulphated and N-reacetylated heparin, desulphated and N-reacetylated heparin, N-carboxymethylated and/or partially N-acetylated chitosan, polyacrylic acid, polyvinylpyrrolidone, polyethylene glycol and/or mixtures of these substances. These stents with a hemocompatible coating are prepared by providing conventional normally non coated stents and by preferably covalent deposition of a hemocompatible layer which permanently masks the surface of the implant after the release of the active agent and thus, after the decay of the active agent's influence and the degradation of the matrix.

The conventional stents which can be coated according to the inventive methods, consist of stainless steel, nitinol or other metals and alloys or of synthetic polymers.

Another preferred embodiment of the stents according to invention shows a coating which consists of at least two layers. Multiple layer systems are used as well. In such multiple layer systems the layer which is directly deposited on the stent is labelled first layer. Labelled second layer is that layer which is deposited on the first layer, etc.

According to the two layer design the first layer consists of a hemocompatible layer which is substantially covered completely by a biodegradable layer which comprises at least an antiproliferative, antiphlogistic and/or antithrombotic active agent bound covalently and/or adhesively. Also applied are active agent combinations which mutually facilitate and replenish themselves.

As biodegradable substances for the external layer can be used: polyvalerolactones, poly-e-decalactones, polylactonic acid, polyglycolic acid, polylactides, polyglycolides, copolymers of the polylactides and polyglycolides, poly-e-caprolactone, polyhydroxybutanoic acid, polyhydroxybutyrates, polyhydroxyvalerates, polyhydroxybutyrate-co-valerates, poly(1,4-dioxane-2,3-diones), poly(1,3-dioxane-2-ones), poly-p-dioxanones, polyanhydrides such as polymaleic anhydrides, polyhydroxymethacrylates, fibrin, polycyanoacrylates, polycaprolactonedimethylacrylates, poly-b-maleic acid, polycaprolactonebutylacrylates, multiblock polymers such as from oligocaprolactonedioles and oligodioxanonedioles, polyether ester multiblock polymers such as PEG and polybutyleneterephtalate, polypivotolactones, polyglycolic acid trimethyl-carbonates, polycaprolactoneglycolides, poly-g-ethylglutamate, poly(DTH-iminocarbonate), poly(DTE-co-DT-carbonate), poly(bisphenol-A-iminocarbonate), polyorthoesters, polyglycolic acid trimethylcarbonates, polytrimethylcarbonates, polyiminocarbonates, poly(N-vinyl)-pyrrolidone, polyvinylalcoholes, polyesteramides, glycolated polyesters, polyphosphoesters, polyphosphazenes, poly[p-carboxyphenoxy)propane], polyhydroxypentanoic acid, polyanhydrides, polyethyleneoxidepropyleneoxide, soft polyurethanes, polyurethanes with amino acid residues in the backbone, polyether esters such as polyethyleneoxide, polyalkeneoxalates, polyorthoesters as well as copolymers thereof, lipides, carrageenanes, fibrinogen, starch, collagen, protein based polymers, polyamino acids, synthetic polyamino acids, zein, modified zein, polyhydroxyalkanoates, pectic acid, actinic acid, modified and non modified fibrin and casein, carboxymethylsulphate, albumin, moreover hyaluronic acid, heparan sulphate, heparin, chondroitinesulphate, dextran, b-cyclodextrines, copolymers with PEG and polypropyleneglycol, gummi arabicum, guar, gelatine, collagen, collagen-N-hydroxysuccinimide, lipides, phospholipides, modifications and copolymers and/or mixtures of the afore mentioned substances.

The layer and layers respectively which contain the active agent is slowly degradated by components of the blood such that the active agent is released of the external layer according to the degradation velocity or resolves itself from the matrix according to its elution behavior. The first hemocompatible layer guarantees the required blood compatibility of the stent once the biodegradable layer is degraded. This biological degradation of the external layer and the corresponding release of the active agent reduces strongly an ongrowth of cells only for a certain period of time and an aimed controlled adhesion is enabled where the external layer has been already widely degradated. The biological degradation of the external layer spans advantageously from 1 to 36 months, preferably from 1 to 6 months, especially preferred from 1 to 2 months. It was shown that suchlike stents prevent or at least very strongly reduce restenosis. In this period of time the important healing processes take place. Finally the hemocompatible layer remains as athrombogeneous surface and masks the foreign surface in such a way that no life-threatening reaction can occur anymore.

Suchlike stents are preparable via a method for the hemocompatible coating of stents the basis of which is formed by the following principle:
 a) providing a non coated stent,
 b) deposition of a preferred covalently bound hemocompatible layer,
 c) substantially complete coating of the hemocompatible layer via dipping or spraying method with at least one active agent, or
 c') substantially complete coating and/or incomplete coating of the hemocompatible layer via dipping or spraying method with at least one biodegradable and/or biostable layer which comprises at least one active agent and/or represents the active agent itself.

The principle of coating offers a big range of variation concerning the contrived requirements for the active agent and is separable into different coating types which can be combined also among themselves.

Coating Principle I:
 a) providing a non coated stent,
 b) deposition of a hemocompatible layer,
 c) deposition of an active agent or an active agent combination on the hemocompatible layer without a matrix,
 d) deposition of an active agent or an active agent combination on the hemocompatible layer without a matrix and substantially complete and/or incomplete coating of the layers with a biodegradable and/or biostable material for diffusion control.

Coating Principle II:
a) providing a non coated stent,
b) deposition of a hemocompatible layer,
c) substantially complete coating and/or incomplete coating of the hemocompatible layer with at least one biodegradable and/or biostable layer which comprises at least one active agent bound covalently and/or adhesively to the hemocompatible layer,
d) substantially complete coating of the hemocompatible layer with at least one biodegradable and/or biostable layer which comprises at least one active agent bound covalently and/or adhesively to the matrix and another biodegradable and/or biostable layer without an active agent as diffusion barrier which covers the subjacent layer completely and/or partially.

Coating Principle III:
a) providing a non coated stent,
b) deposition of a hemocompatible layer,
c) substantially complete coating of the hemocompatible layer with at least one biodegradable and/or biostable layer which comprises at least one active agent bound covalently and/or adhesively,
d) deposition of an active agent or an active agent combination bound covalently and/or adhesively to the subjacent layer,
e) substantially complete coating of the hemocompatible layer with at least one biodegradable and/or biostable layer which comprises at least one active agent bound covalently and/or adhesively, deposition of an active agent or an active agent combination and another biodegradable and/or biostable layer without an active agent as diffusion barrier which covers the subjacent layer completely and/or partially.

Coating Principle IV:
a) providing a non coated stent,
b) deposition of a hemocompatible layer,
c) substantially complete and/or incomplete coating of the hemocompatible layer with at least two biodegradable and/or biostable layers which comprise covalently and/or adhesively at least one active agent in a different concentration per layer,
d) substantially complete and/or incomplete coating of the hemocompatible layer with at least two biodegradable and/or biostable layers which comprise at least one active agent bound covalently and/or adhesively in a different concentration per layer and at least another biodegradable and/or biostable layer without an active agent as diffusion barrier which covers the subjacent layer completely and/or partially,
e) substantially complete and/or incomplete coating of the hemocompatible layer with at least one biodegradable and/or biostable layer which comprises at least one active agent and/or at least another active agent of the same group or from another group of complementary properties in the same or different concentrations in a covalent and/or adhesive form,
f) substantially complete and/or incomplete coating of the hemocompatible layer with at least two biodegradable and/or biostable layers which comprise at least one active agent and/or at least another active agent of the same group or from another group of complementary properties in the same or different concentrations and at least another biodegradable and/or biostable layer without an active agent as diffusion barrier which covers the subjacent layer completely and/or partially,
g) substantially complete coating of the hemocompatible layer with at least two biodegradable and/or biostable layers which comprise covalently and/or adhesively at least one active agent in the same and/or different concentrations and another biodegradable and/or biostable layer without an active agent as diffusion barrier which covers the subjacent layer completely or also just partially and whereas that layer is covered by an active agent layer which consists of at least one active agent bound covalently and/or adhesively without a matrix.

Another advantageous embodiment is represented by a stent with an at least three layered coating, whereas the first layer covers the surface of the stent with the hemocompatible layer, the second layer contains the active agent and is not biodegradable and is covered by a third hemocompatible layer. The external layer provides the stent herein the necessary blood compatibility and the second layer serves as an active agent reservoir. The active agent which is if needed covalently bound to the matrix via a hydrolysis-weak bonding and/or added in a solvent dissolved matrix which is required for the coating method, is thus released from the second layer continuously and in small concentrations and diffuses uninhibited through the external hemocompatible layer. This layer assembly also yields the result that the population of the stent surface with cells is not prevented but is reduced to an ideal degree. The first layer offers a risk minimization for eventually occurring damages of the coated stent surface during the implantation e.g. by abrasions through the present plaque or during the prearrangement e.g. during the crimping. A second security guarantee results from the fact that even a biostable polymer is degradated in the body over a more or less long period of time which at least partially uncovers the stent surface.

Combinations especially with biodegradable material as described in the coating principles are possible, too.

Suchlike stents can be prepared by providing a conventional stent, depositing a hemocompatible first layer on its surface, depositing a non biodegradable layer which at least comprises one active agent as well as combinations with other active agents from other groups bound covalently and/or adhesively and coating of this layer substantially completely with another hemocompatible layer.

Substances which come into question for the biostable layer are all of the consistent materials used in medical science, thereto are accounted: polyacrylic acid and polyacrylates such as polymethylmethacrylate, polybutyl methacrylate, polyacrylamide, polyacrylonitriles, polyamides, polyetheramides, polyethylenamine, polyimides, polycarbonates, polycarbourethanes, polyvinylketones, polyvinylhalogenides, polyvinylidenhalogenides, polyvinyl ethers, polyvinylaromates, polyvinyl esters, polyvinylpyrrolidones, polyoxymethylenes, polyethylene, polypropylene, polytetrafluoroethylene, polyurethanes, polyolefin elastomers, polyisobutylenes, EPDM gums, fluorosilicones, carboxymethyl chitosan, polyethylenterephthalate, polyvalerates, carboxymethylcellulose, cellulose, rayon, rayon triacetates, cellulose nitrates, cellulose acetates, hydroxyethylcellulose, cellulosebutyrates, celluloseacetatebutyrates, ethylvinylacetate copolymers, polysulphones, epoxy resins, ABS resins, EPDM gums, silicones such as polysiloxanes, polyvinylhalogenes and copolymers, cellulose ethers, cellulose triacetates, chitosan and copolymers and/or mixtures of these substances.

In case of multi layer systems the newly deposited layer covers the subjacent layer substantially completely.

The stents according to invention solve both the problem of acute thrombosis and the problem of neointima hyperplasia after a stent implantation. In addition the stents according to invention are well suitable due to their coating whether as single layer or as multi layer system especially for the continuous release of one or more antiproliferative and/or immunosuppressive active agents. Due to this feature of aimed continuous active agent release in a required amount the coated stents according to invention prevent almost completely the danger of restenosis.

EXAMPLES

Example 1

Covalent Hemocompatible Coating of Stents:
Not expanded stents of medicinal stainless steel LVM 316 were degreased in the ultrasonic bath for 15 minutes with acetone and ethanol and dried at 100° C. in the drying closet. Then they were dipped for 5 minutes into a 2% solution of 3-aminopropyltriethoxysilane in a mixture of ethanol/water (50/50: (v/v)) and then dried for 5 minutes at 100° C. Afterwards the stents were washed with demineralized water over night.

Example 2

3 mg desulphated and reacetylated heparin were dissolved at 4° C. in 30 ml 0.1 M MES-buffer (2-(N-morpholino) ethanesulphonic acid) pH 4.75 and mixed with 30 mg N-cyclohexyl-N'-(2-morpholinoethyl)carbodiimide-methyl-p-toluenesulphonate. In this solution 10 stents were stirred for 15 hours at 4° C. Then they were rinsed with water, 4 M NaCl solution and water in each case for 2 hours.

Example 3

Determination of the Glucosamine Content of the Coated Stents by HPLC:
Hydrolysis: the coated stents are given in small hydrolysis tubes and are abandoned with 3 ml 3 M HCl for exactly one minute at room temperature. The metal probes are removed and the tubes are incubated after sealing for 16 hours in the drying closet at 100° C. Then they are allowed to cool down, evaporated three times until dryness and taken up in 1 ml degassed and filtered water and measured contra an also hydrolysed standard in the HPLC:

| stent | sample area | desulphat. + reacet. heparin [g/sample] | area [cm$^2$] | desulphat. + reacet. heparin [g/cm2] | desulphat. + reacet. heparin [pmol/cm$^2$] |
|---|---|---|---|---|---|
| 1 | 129.021 | 2.70647E−07 | 0.74 | 3.65739E−07 | 41.92 |
| 2 | 125.615 | 2.63502E−07 | 0.74 | 3.56084E−07 | 40.82 |
| 3 | 98.244 | 1.93072E−07 | 0.74 | 2.60908E−07 | 29.91 |
| 4 | 105.455 | 2.07243E−07 | 0.74 | 2.80058E−07 | 32.10 |
| 5 | 119.061 | 2.33982E−07 | 0.74 | 3.16192E−07 | 36.24 |
| 6 | 129.202 | 2.53911E−07 | 0.74 | 3.43124E−07 | 39.33 |
| 7 | 125.766 | 2.53957E−07 | 0.74 | 3.43185E−07 | 39.34 |

Example 4

Experiments Concerning the Coating of Surfaces with Tacrolimus:
Pre-Experiments with Toluidine Blue:
First pre-experiments are carried out with toluidine blue (Aldrich) since tacrolimus can be detected chemically quite difficult.

| Chemicals: | |
|---|---|
| stainless steel tubes LVM 316 | 2.5 cm in length, 2 mm in diameter |
| polylactide | Fluka, Lot. 398555/123500, HNo. 0409 |
| toluidine blue | Aldrich, Lot. 19,816-1, HNo. 0430 |
| PBS-buffer pH 7.4 | 14.24 g Na$_2$HPO$_4$, 2.72 g NaH$_2$PO$_4$ and 9 g NaCl |

Realization:
The stent is weighed out on the analytical balance and the weight is noted. In a small hydrolysis tube 0.5 g polylactide are dissolved in 2 ml of CHCl$_3$. Therefore, it is heated to 65° C. in the water bath. The solution is cooled down in the freezing compartment. Thereto are added 200 μg toluidine blue in 200 μl of CHCl$_3$. The stent is dipped into this solution. After a couple of minutes the stent is taken out of the solution with tweezers and moved within the fume hood until the solvent evaporates. After air drying the stent is freeze dried for about 10 min. After the drying the stent is balanced again. The amount of the immobilized polylactide with toluidine blue is measured from the weight difference (sample 1).

This experiment is repeated another time with the same solution (sample 2).

For sample 3 the dipping solution (1.93 ml) which results from experiment 1 (sample 1) and experiment 2 (sample 2) is mixed with 0.825 mg toluidine blue in 0.825 ml of CHCl$_3$ and 250 mg polylactide. The polylactide is dissolved during heating. Then a stent is dipped into it two times as described above.

Results:
The untreated stents had a weight of 176.0 mg and 180.9 mg. After dipping into the polylactide solution the stents balanced 200.9 and 205.2 mg.

The dipping solution contains 500 mg polylactide and 200 μg toluidine blue. The bound amount of toluidine blue can be measured for the samples 1 and 2 from this ratio. In case of sample 3 2.755 ml solution contain 1 mg toluidine blue and 638.6 mg polylactide (initial weight—consumption sample 1+2; approx. 50 mg). Here two stents are given into one preparation to obtain higher absorptions. As the dipping solution was very viscous which yielded a very thick coating it was diluted from 2.625 ml with chloroform to 4 ml.

Concentrations in the Dipping Solution:

| sample | volume (ml) | c (polylactide mg/ml) | c (toluidine blue μg/ml) |
|---|---|---|---|
| 1 | 2.2 | 227.3 | 90.9 |
| 2 | 2.2 | 227.3 | 90.9 |
| 3 | 2.755 | 231.8 | 363.0 |
| 4 | 4.0 | 134.5 | 212.5 |

Weight of the Tubes and the Resultant Measured Coating:

| sample | net weight | total weight | PL & toluidine blue | Toluidine blue |
|---|---|---|---|---|
| 1 | 176.0 mg | 200.9 mg | 24.9 mg | 9.96 μg |
| 2 | 180.9 mg | 205.2 mg | 24.3 mg | 9.72 μg |
| 3 | 317.2 mg | 410.8 mg | 93.6 mg | 135.73 μg |
| 4 | 180.8 mg | 194.8 mg | 14.8 mg | 23.38 μg |

Example 5

Elution Behavior of the Coatings with Different Concentrations:

As pre-experiment a UV-Vis spectra of a toluidine blue solution in ethanol is taken (c=0.1 mg/ml) and the absorption maximum is determined. The toluidine blue concentration in the solution is measured at an absorption maximum of 627 nm. Thereto a calibration curve is generated.

A stent is hung into a beaker with 25 ml of physiological sodium chloride solution in a phosphate buffer pH 7.4 (14.24 g $NaH_2PO_4$, 2.72 g $K_2HPO_4$ and 9 g NaCl) and stirred gently at room temperature. After 0.5, 1, 2, 3, 6, 24, 48 and 120 hours, each time a sample of 3 ml is taken, measured spectroscopically and given back into the preparation.

| time/h | abs. s1 | c (ng/ml) | abs. s2 | c (ng/ml) | abs. s3 | c (ng/ml) | abs. s4 | c (ng/ml) |
|---|---|---|---|---|---|---|---|---|
| 0 | 0.0002 | 0 | −0.0002 | 0 | 0.0036 | 0 | 0.0063 | 0 |
| 0.5 | −0.0011 | 0 | 0.0011 | 6.4 | 0.0095 | 29.2 | 0.0125 | 30.7 |
| 1 | 0.0003 | 0.5 | 0.0014 | 7.9 | 0.0164 | 63.3 | 0.0121 | 28.7 |
| 2 | 0.0007 | 2.5 | 0.0008 | 5.0 | 0.0256 | 108.9 | 0.0131 | 33.7 |
| 3 | −0.0004 | 0 | 0.0006 | 4.0 | 0.0294 | 127.7 | 0.0136 | 36.1 |
| 6 | 0.0013 | 5.4 | 0.0015 | 8.4 | 0.0333 | 147.0 | 0.0142 | 39.1 |
| 24 | 0.0017 | 7.4 | 0.0020 | 10.8 | 0.0527 | 246.0 | 0.0239 | 176 |
| 48/96 | 0.0024 | 10.9 | 0.0033 | 17.3 | 0.1096 | 524.8 | 0.0147 | 41.6 |
| 120 | 0.0017 | 7.4 | 0.0038 | 19.8 | 0.1110 | 531.7 | 0.0161 | 48.5 |

Absorption of the samples after different periods of time. For measuring of the concentration the cuvette difference (abs. at T=0) is subtracted from the measured value.

After 12 and 13 days respectively the experiment was terminated. On all of the stents after the expiration of the experiment a coating was still present. For determining the amounts of toluidine blue and polylactide respectively which were dissolved, the stents were rinsed with water and ethanol and then freeze dried during 1 h for balancing them afterwards.

| S. | final weight | initial weight | PL + Tb | diss. PL + Tb | diss. Tb. | rem. Tb. |
|---|---|---|---|---|---|---|
| 1 | 196.5 | 200.9 mg | 24.9 mg | 4.4 mg | 1.76 µg | 8.2 µg |
| 2 | 199.4 | 205.2 | 24.3 mg | 5.8 mg | 2.32 µg | 3.48 µg |
| 3 | 385.4 | 410.8 | 93.6 mg | 25.4 mg | 36.83 µg | 98.8 µg |
| 4 | 191.3 | 194.8 | 14.8 mg | 3.5 mg | 5.52 µg | 17.86 µg |

In case of concentrations of 90 µg toluidine blue per ml dipping solution the released amounts of toluidine blue are so low that the absorptions are at the detection limit of the spectrometer. In case of a concentration of 200 µg/ml the values are after a couple of hours in the measurable area. It is recommended for the measurement to place two samples into a beaker (elution jar) to yield higher absorptions. In case of the highest polylactide/toluidine blue concentration a saturation effect seems to appear while the elution ratio in case of the thinner samples has an almost linear trajectory. On all of the stents the coating can still be detected after several days.

After approx. 2 weeks the bound toluidine blue dissolved in average from about ¼-⅕. Hence it results that the samples still would have eluted toluidine blue for approx. 8 to 10 weeks.

The dipping solution may not be too thick and should be cooled so that the chloroform cannot evaporate too fast during the extraction as else the thickness of the coating becomes too large and inhomogeneous. Here the polylactide concentration in sample 4 (134 mg/ml) seems to be sufficient, above all in case of higher concentrations the solution becomes extremely viscous and the polylactide is only very difficult to dissolve.

Example 6

Coating of the Stents via the Spraying Method:

The according to example 1 and example 2 pre-prepared not expanded stents are balanced and horizontally hung onto a thin metal bar (d=0.2 mm) which is stuck on the rotation axis of the rotation and feed equipment and rotates with 28 r/min. The stents are fixed in such way, that the interior of the stents does not touch the bar. At a feeding amplitude of 2.2 cm and a feeding velocity of 4 cm/s and a distance of 6 cm between stent and spray nozzle, the stent is sprayed with the respective spray solution. After the drying (about 15 minutes) at room temperature and proximately in the fume hood over night it is balanced again.

Example 7

Coating of the Stents with Pure Matrix:
Preparation of the Spray Solution:
176 mg polylactide is balanced and replenished with chloroform to 20 g.

The stents are sprayed in each case with 3 ml of the spraying solution, balanced before and after the spraying and the yielding layer thickness is determined by measuring under the microscope 100-times magnified.

| stent No. | before coating | after coating | weight of coating | layer thickness |
|---|---|---|---|---|
| 1 | 0.0193 g | 0.0205 g | 1.2 mg | 10.4 µm |
| 2 | 0.0193 g | 0.0205 g | 1.2 mg | 10.4 µm |
| 3 | 0.0204 g | 0.0216 g | 1.2 mg | 10.4 µm |
| 4 | 0.0206 g | 0.0217 g | 1.1 mg | 10.4 µm |

Example 8 (FIG. 1)

Coating of the Stents with Pure Active Agent:
Preparation of the Spray Solution:
44 mg taxol are dissolved in 6 g chloroform.
The stents are balanced before and after the spraying.

| stent No. | before coating | after coating | weight of coating |
|---|---|---|---|
| 1 | 0.0194 g | 0.0197 g | 0.30 mg |

Example 9

Determination of the Elution Behaviour in PBS-Buffer:

Each stent placed in a sufficiently small flask, 2 ml PBS-buffer is added, sealed with parafilm and incubated in the drying closet at 37° C. After expiry of the chosen time intervals in each case the supernatant is depipetted and its UV absorption at 306 nm is measured.

Example 10

Coating of the Hemocompatibly Equipped Stents with an Active Agent Loaded Matrix (FIG. 4):

Spray Solution:

Polylactide RG502/taxol - solution is replenished from 145.2 mg polylactide and 48.4 mg taxol to 22 g with chloroform.

| stent | spray solution | weight before (g) | weight after (g) | weight of coating | weight of active agent | active agent µg/mm² | layer thickness |
|---|---|---|---|---|---|---|---|
| 1 | 0.8 ml | 0.02180 | 0.02215 | 0.35 mg | 146 µg | 1.97 | 7.9 µm |
| 2 | 0.8 ml | 0.02105 | 0.02142 | 0.37 mg | 154 µg | 2.08 | 6.7 µm |
| 3 | 0.8 ml | 0.02247 | 0.02285 | 0.38 mg | 158 µg | 2.14 | 9.8 µm |
| 4 | 0.8 ml | 0.02395 | 0.02432 | 0.37 mg | 154 µg | 2.08 | 11.0 µm |
| 5 | 0.8 ml | 0.02247 | 0.02286 | 0.39 mg | 163 µg | 2.20 | 9.1 µm |
| 6 | 0.8 ml | 0.02442 | 0.02482 | 0.40 mg | 167 µg | 2.26 | 12.2 µm |

Example 11

Coating of the Stents with an Active Agent Loaded Matrix and an Active Agent as Topcoat (FIG. 5):

Basis coat: 19.8 mg polylactide and 6.6. mg taxol are replenished with chloroform to 3 g.

Topcoat: 8.8 mg taxol are replenished with chloroform to 2 g.

| stent | spray solution | weight before (g) | weight after (g) | weight of coating | weight of active agent | active agent µg/mm² | layer thickness |
|---|---|---|---|---|---|---|---|
| 1 | 0.85 ml | 0.0235 | 0.0238 | 0.30 mg | 131 µg | 1.56 | 9.7 µm |
| 2 | 0.85 ml | 0.0260 | 0.0264 | 0.40 mg | 175 µg | 2.09 | 10.1 µm |

Example 12

Coating of the Stents with a Polylactide which Contains a Hydrophilic Active Agent and with an Active Agent Free Matrix as Topcoat (FIG. 6):

Spray Solutions:

Basis coating: 22 mg polylactide and 22 mg hydrophilic active agent are balanced and replenished with chloroform to 5 g.

Topcoat: 22 mg polylactide and 22 mg polystyrene are balanced and replenished with chloroform to 5 g.

| spray solution | before coating | after coating | weight of coating | weight of active agent |
|---|---|---|---|---|
| 0.85 ml | 0.0135 g | 0.0143 g | 0.8 mg | 200 µg |

Example 13

Hemocompatibility of the Used Matrix:

4 coronary stents: 2 untreated, 2 coated, not sterilized

Label: K3, K4 are coated

K5, K6 are untreated

The following measuring parameters were determined:

Hemogram

Platelet factor 4 (PF4)

Complement factor 5a (C5a)

Thrombin-Antithrombin (TAT)

Carrying Out of the Experiment:

Donor blood is taken up into 1.5 U/ml of heparin. The stents are introduced into PVC tubes (I.D. 3.5 mm, L=95 cm) and fixed via balloon catheter. The 4 tubes (K3-K6) and two empty tubes (L1, L2) are filled in each case with 7.5 ml isotonic sodium chloride solution and rotated for 15 minutes at 5 r/min at 37° C. in the Chandler loop. The completely emptied tubes are filled carefully with heparinated donor blood (7.5 ml) and rotated for 60 min at 5 r/min. Accordingly to the anticoagulants samples are taken in monovettes and sample jars respectively (PF4-CTAD, TAT-citrate, C5a-EDTA, BB-EDTA) and processed.

Results (see FIG. 8-10):

The determination of the platelet number shows no significant difference between the empty control tubes, the coated and non coated stents. The released PF4 is in case of the coated and non coated tubes at the same level. The determination of the activated complement factor 5 (C5a) shows in case of the coated stents a smaller activation as in case of the non coated stents. The measurement of the TAT-values lacks due to organizational reasons. These samples are stored at −80° C.

Example 14

Determination of the restenosis rate in the animal experiment (FIG. 10):

Young porks in the age of 6-8 months were provided with 4 stents in each case. One untreated stent was compared to a stent which was coated with a polyacrylic acid and with 2 hemocompatible substances bound covalently to the stent surface. In case of the one substance a semi-synthetic heparin derivative is concerned, the other substance is the oligo- and polysaccharides of the glycocalix which was taken from the erythrocyte surface. After four weeks the animals are euthanized and the restenosis rate is determined.

Figure 1:
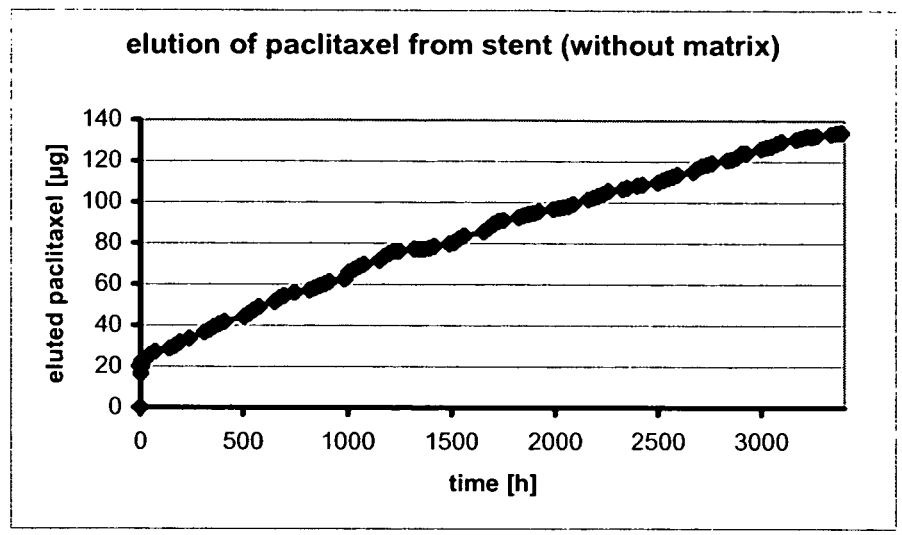
FIG. 1: Elution diagram of paclitaxel from the stent (without matrix).
Figure 2:
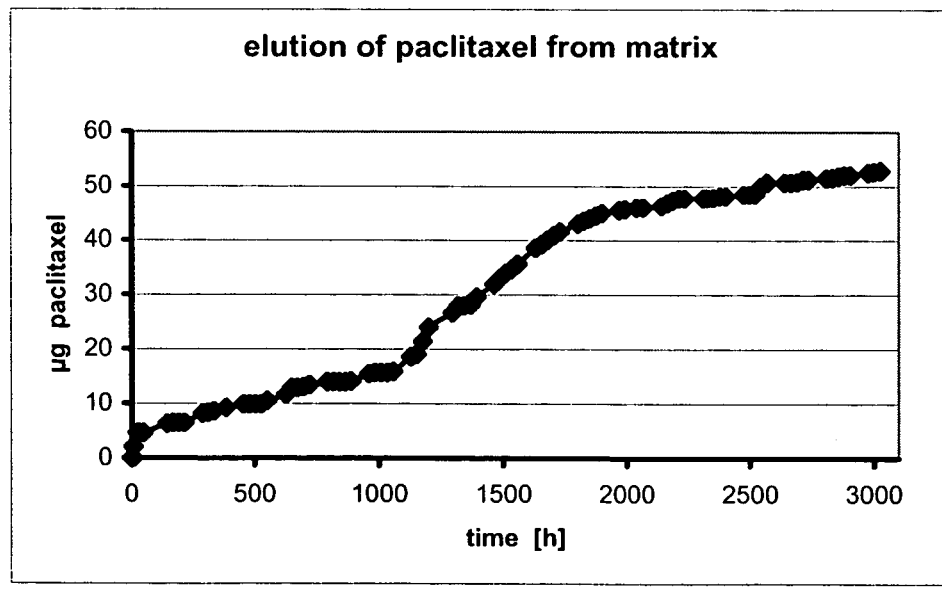
FIG. 2: Elution diagram of paclitaxel embedded into matrix.
Figure 3:
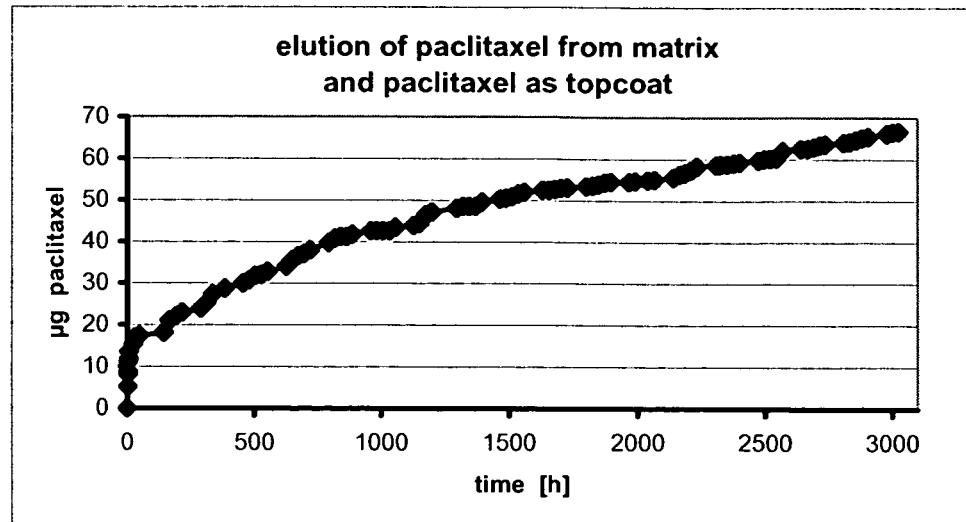
FIG. 3: Elution diagram of paclitaxel embedded into matrix and of a layer of undiluted paclitaxel which covers the basis coating completely.
Figure 4:
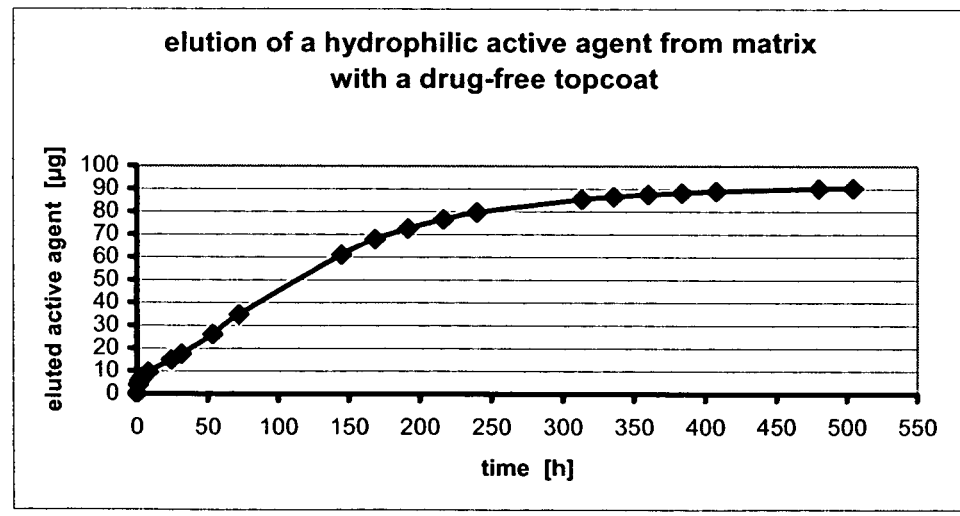
FIG. 4: Elution diagram of a hydrophilic substance embedded into the matrix and of a suprajacent polymer (topcoat) which covers the basis coating completely for diffusion control.
Figure 5:
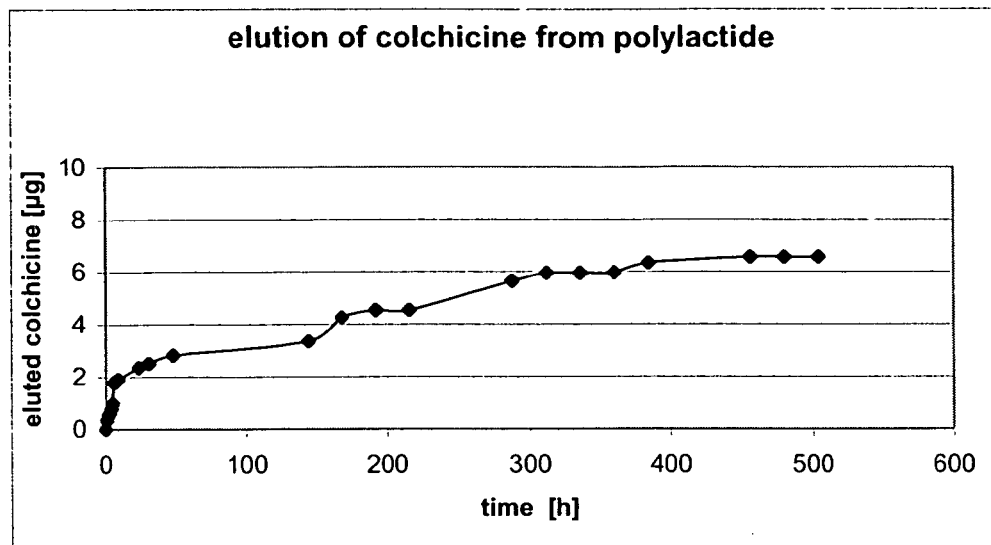
FIG. 5: Elution diagram of colchicine from matrix.
Figure 6:
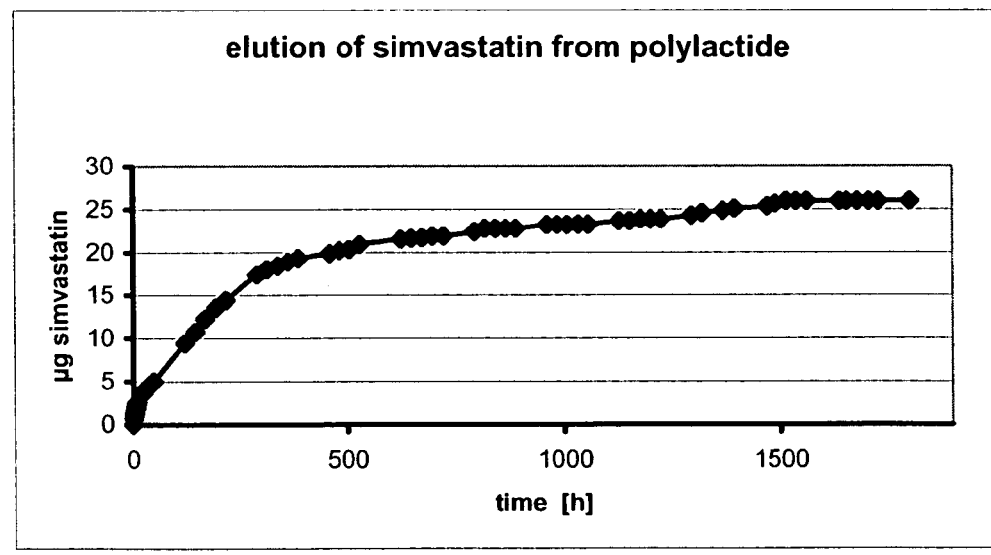
FIG. 6: Elution diagram of simvastatin from matrix.
Figure 7:
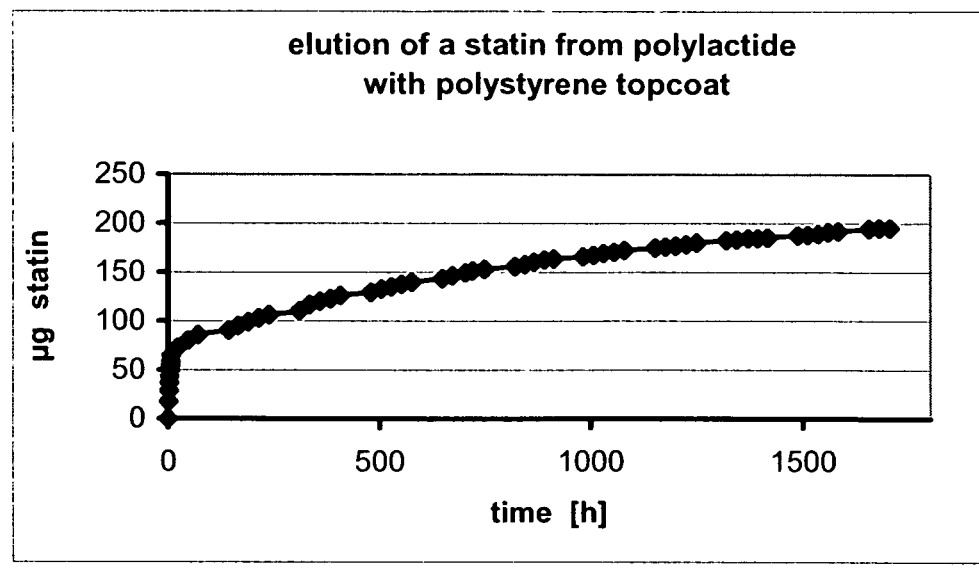
FIG. 7: Elution diagram of a statin from the matrix with polystyrene which covers the basis coating as diffusion control completely.
Figure 8:
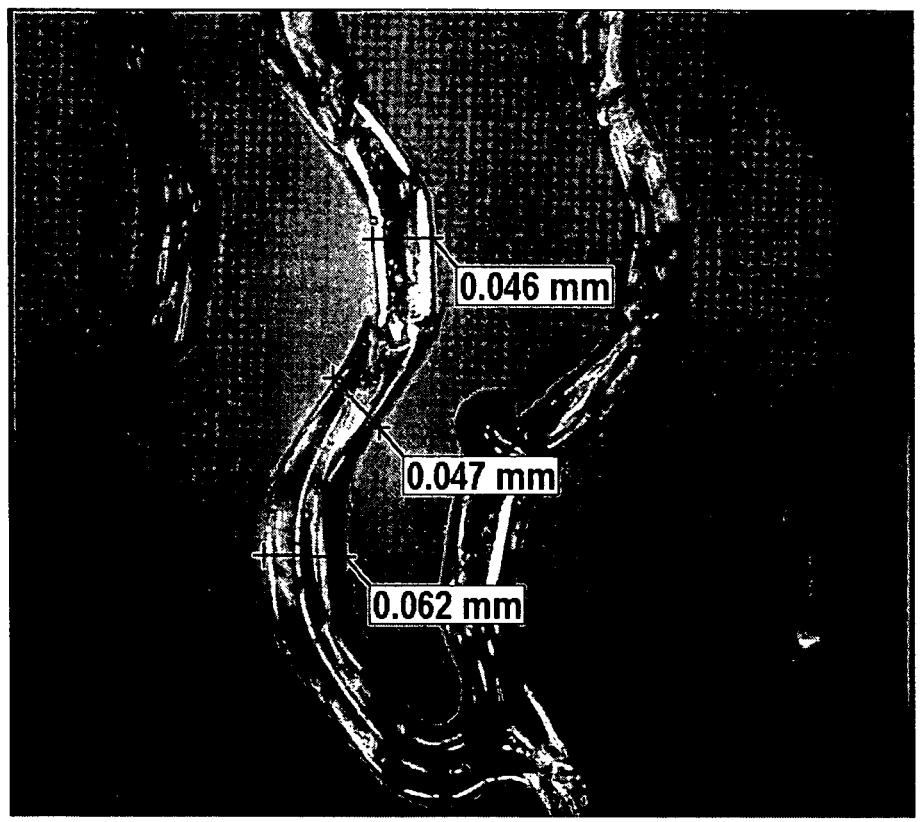
FIG. 8: View of a polymer coated stent. For marking the coating it is scratched at one location and beneath the surface of the stent is clearly visible.
Figure 9:
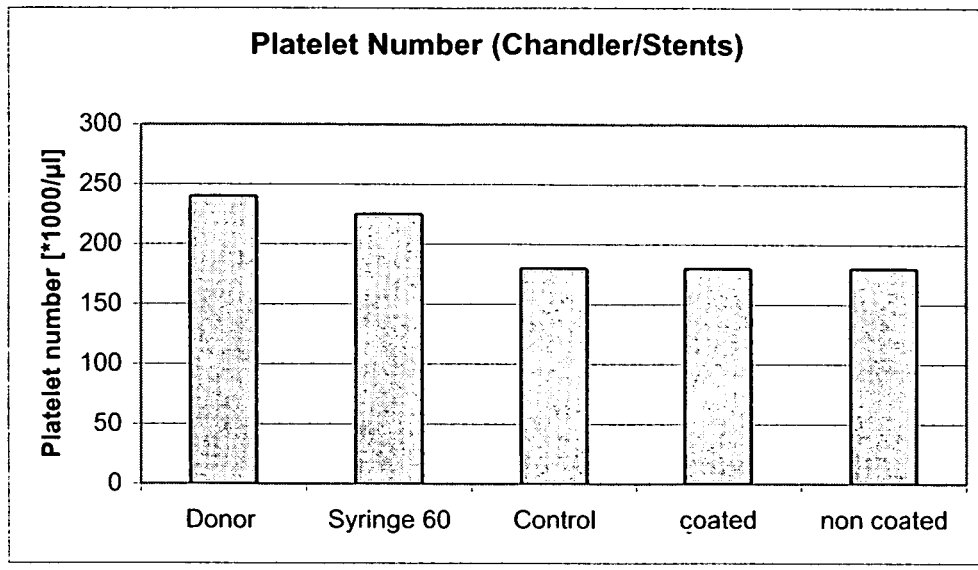
FIG. 9: Comparison of the platelet number in the blood after Chandler loop between coated and non coated stent as regards the empty tube (control), the platelet number of freshly extracted blood (donor) and the storage of 60 min in the syringe (syringe 60').
Figure 10:
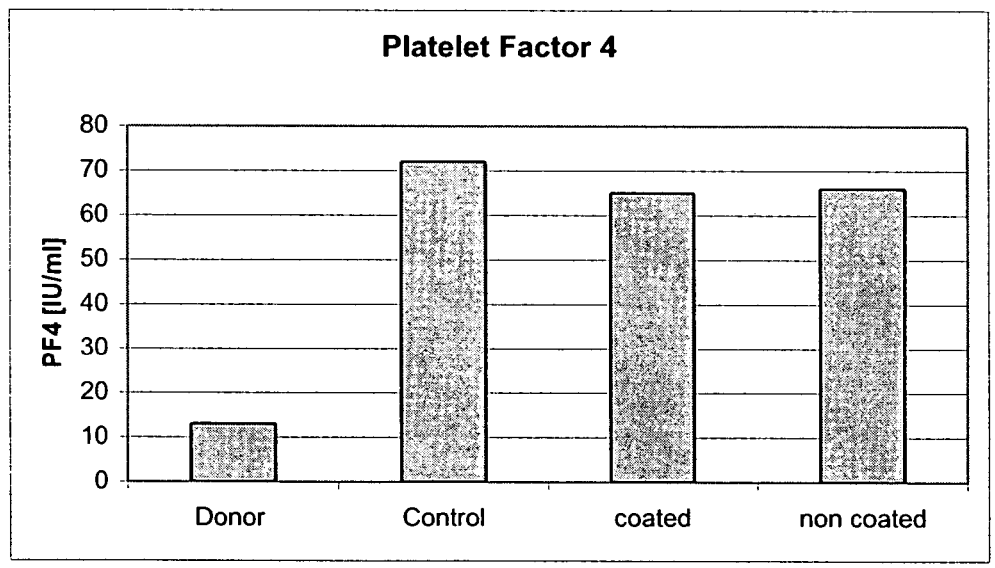
FIG. 10: Comparison of the platelet factor 4 concentration in the freshly extracted blood (donor), in the empty tube (control) after 60 minutes and non coated stents with coated stent.
Figure 11:
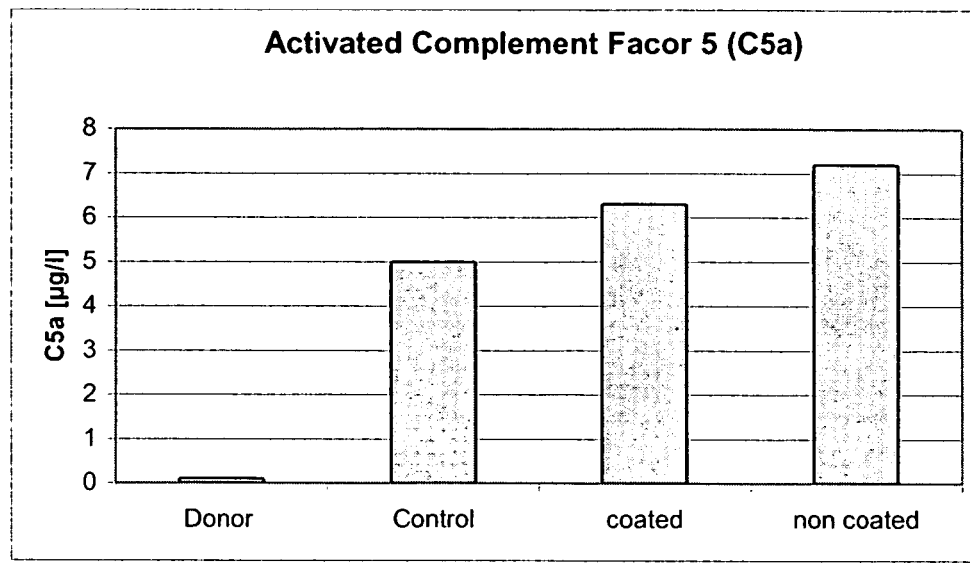
FIG. 11: Comparing diagram to the activated complement factor C5a in the freshly extracted blood (donor), in the empty tube (control) after 60 minutes and non coated stents with coated stent.
Figure 12:
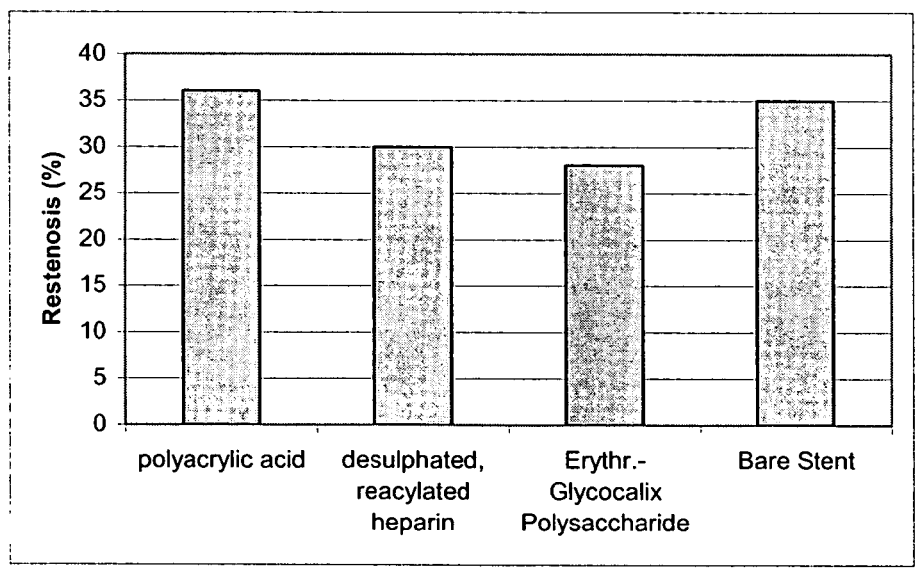
FIG. 12: Schematic presentation of the restenosis rate of with completely desulphated and N-reacetylated heparin covalently coated stents and with oligo- and polysaccharides of the erythrocytic glycocalix coated stents in comparison to the non coated stent and with polyacrylic acid coated stents (after 4 weeks of implantation time in the pork).

The invention claimed is:

1. A stent coated with a hemocompatible layer consisting of completely desulphated and N-reacetylated heparin, whereas the hemocombatible layer is bound covalently on the stent surface and at least a second adjacent layer which comprises at least one antiproliferative, anti-inflammatory and/or antithrombotic active agent covalently and/or adhesively bound.

2. Stent according to claim 1 wherein the active agents are chosen from the group which contains sirolimus, everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, 13-lapachone, podophyllotoxin, betulin, podophyllic acid 2-ethylhydrazide, peginterferon a-2b, filgrastim, macrogol, dacarbazine, basiliximab, daclizumab, selectin, CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors, pentaerythritol tetranitrate and syndnoeimines, S-nitrosoderivatives, tamoxifen, staurosporine, 13-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors, cyclosporine A, paclitaxel, 6-a-hydroxy-paclitaxel, baccatin, taxotere and other both synthetically and from native sources obtained macrocyclic oligomers of carbon suboxide and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, 13-sitosterin, ademetionine, myrtecaine, polidocanol, nonivamide, levomenthol, benzocaine, aescin, ellipticine, indibulin, colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-I, plasminogen activator inhibitor-2, antisense oligonucleotides, VEGF inhibitors, IGF-1, active agents from the group of antibiotics, cefadroxil, cefazolin, cefaclor, cefotaxim, tobramycin, gentamycin, penicillins, dicloxacillin, oxacillin, sulfonamides, metronidazol, antithrombotics, argatroban, acetylsalicylsaure, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators, dipyramidole, trapidil, nitroprussides, PDGF antagonists, triazolopyrimidine and seramin, ACE inhibitors, captopril, cilazapril, lisinopril, enalapril, losartan, thiolprotease inhibitors, prostacyclin, vapiprost, interferon a, β and γ, histamine antagonists, serotonin blockers, apoptosis inhibitors, apoptosis regulators, p65 NF-kB, Bcl-xL antisense oligonucleotides, halofuginone, nifedipine, tocopherol, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamid, retinoic acid, quinidine, disopyramide, flecamide, propafenone, sotalol, amidorone, natural and synthetically obtained steroids, bryophyllin A, inotodiol, maquiroside A, ghalakinoside, mansonine, strebloside, hydrocortisone, betamethasone, dexamethasone, non-steroidal anti-inflammatory substances, fenoprofen, ibuprofen, indomethacin, naproxen, phenylbutazone and other antiviral agents, acyclovir, ganciclovir and zidovudine, antimycotics, clotrimazole, flucytosine, griseofulvin, ketoconazole, miconazole, nystatin, terbinafine, antiprozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-13-hydroxypregnadien-3,20-dione, bilobol, ginkgol, ginkgolic acid, helenalin, indicine, indicine-N-oxide, lasiocarpine, inotodiol, glycoside I a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-All, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, vismione A and B.

3. Stent according to claim 1 wherein the antiproliferative, antiinflammatory and/or antithrombotic active agent is comprised in a pharmaceutically active concentration of 0.001-10 mg per cm2 stent surface.

4. Stent according to claim 1 wherein the coating comprises two or more layers, whereas the first layer is deposited directly onto the stent surface.

5. Stent according to claim 4 wherein the first layer comprises a hemocompatible layer which is coated completely or incompletely with a biodegradable and/or biostable layer that comprises at least one active agent in a covalently and/or adhesively bound form.

6. Stent according to claim 4 wherein the second layer comprises a non biodegradable layer which comprises at least one active agent in a covalently and/or adhesively bound form and which is substantially completely coated with a covalently bound hemocompatible layer.

7. Stent according to claim 5 wherein polyvalerolactones, poly-e-decalactones, polylactic acid, polyglycolic acid, polylactides, polyglycolides, copolymers of the polylactides and polyglycolides, poly-e-caprolactone, polyhydroxybutanoic acid, polyhydroxybutyrates, polyhydroxyvalerates, polyhydroxybutyrate-co-valerates, poly(1,4-dioxane-2,3-diones), poly(1,3-dioxane-2-one), poly-para-dioxanones, polyanhydrides, polymaleic anhydrides, polyhydroxymethacrylates, fibrin, polycyanoacrylates, polycaprolactonedimethylacrylates, poly-β-maleic acid, polycaprolactonebutylacrylates, multiblock polymers, polyetherester multiblock polymers, polypivotolactones, polyglycolic acid trimethylene-carbonates, polycaprolactone-glycolides, poly(g-ethylglutamate), poly(DTH-iminocarbonate), poly(DTE-co-DT-carbonate), poly(bisphenol-A-iminocarbonate), polyorthoesters, polyglycolic acid trimethylene-carbonates, polytrimethylcarbonates, polyiminocarbonates, poly(N-vinyl)-pyrrolidone, polyvinylalcohols, polyesteramides, glycolated polyesters, polyphosphoesters, polyphosphazenes, poly[p-carboxyphenoxy)propane], polyhydroxypentanoic acid, polyanhydrides, polyethyleneoxide-propyleneoxide, soft polyurethanes, polyurethanes with amino acid rests in the backbone, polyetheresters, polyalkeneoxalates, polyorthoesters as well as copolymers thereof, lipids, carrageenans, fibrinogen, starch, collagen, protein based polymers, polyamino acids, synthetic polyamino acids, zein, modified zein, polyhydroxyalkanoates, pectic acid, actinic acid, modified and non modified fibrin and casein, carboxymethylsulphate, albumin, moreover hyaluronic acid, heparan sulphate, heparin, chondroitine sulphate, dextran, b-cyclodextrins, copolymers with PEG and polypropylene glycol, gum arabic, guar, gelatine, collagen, collagen-N-hydroxysuccinimide, lipids, phospholipids, modifications and copolymers and/or mixtures of the afore mentioned substances are used as biodegradable substances for the biodegradable layer.

8. Stent according to claim 5 wherein polyacrylic acid and polyacrylates, polymethylmethacrylate, polybutyl methacrylate, polyacrylamide, polyacrylonitriles, polyamides, polyetheramides, polyethylenamine, polyimides, polycarbonates, polycarbourethanes, polyvinylketones, polyvinylhalogenides, polyvinylidenhalogenides, polyvinyl ethers, polyisobutylenes, polyvinylaromates, polyvinylesters, polyvinylpyrrolidones, polyoxymethylenes, polytetramethyleneoxide, polyethylene, polypropylene, polytetrafluoroethylene, polyurethanes, polyetherurethanes, silicone-polyetherurethanes, silicone-polyurethanes, silicone-polycarbonate-urethanes, polyolefin elastomers, polyisobutylenes, EPDM gums, fluorosilicones, carboxymethyl chitosan, polyaryletherether ketones, polyetherether ketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethylvinylacetate copolymers, polysulphones, epoxy resins, ABS resins, EPDM gums, silicones, polysiloxanes, polydimethylsiloxanes, polyvinyl halogens and copolymers, cellulose ethers, cellulose triacetates, chitosan and copolymers and/or mixtures thereof are used as biostable substances for the biostable layer.

* * * * *